(12) United States Patent
Hulse et al.

(10) Patent No.: US 8,846,754 B2
(45) Date of Patent: Sep. 30, 2014

(54) AZEOTROPE-LIKE COMPOSITIONS OF CIS-1,1,1,4,4,4-HEXAFLUORO-2-BUTENE

(75) Inventors: Ryan Hulse, Getzville, NY (US); Rajiv Ratna Singh, Getzville, NY (US); Martin R. Paonessa, N. Niagra Falls, NY (US); Hang T. Pham, Amherst, NY (US); Mary Bogdan, Morristown, NJ (US); Cliff Gittere, Morristown, NJ (US); Martin Cheney, Morristown, NJ (US); Linda L. Cheney, legal representative, Morristown, NJ (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 12/967,522

(22) Filed: Dec. 14, 2010

(65) Prior Publication Data
US 2012/0004299 A1    Jan. 5, 2012

Related U.S. Application Data

(60) Provisional application No. 61/287,041, filed on Dec. 16, 2009.

(51) Int. Cl.
| | | |
|---|---|---|
| *A01N 43/20* | (2006.01) | |
| *A01N 43/24* | (2006.01) | |
| *A61K 31/335* | (2006.01) | |
| *C07C 21/18* | (2006.01) | |
| *C08J 9/14* | (2006.01) | |
| *A62D 1/00* | (2006.01) | |
| *C09K 3/30* | (2006.01) | |
| *C09K 5/04* | (2006.01) | |

(52) U.S. Cl.
CPC . *C09K 3/30* (2013.01); *C07C 21/18* (2013.01); *C08J 9/149* (2013.01); *A62D 1/0057* (2013.01); *C09K 2205/22* (2013.01); *C09K 2205/122* (2013.01); *C09K 2205/126* (2013.01); *C08J 2207/04* (2013.01); *C09K 2205/108* (2013.01); *C09K 2205/102* (2013.01); *C09K 5/045* (2013.01); *C08J 9/146* (2013.01)
USPC ........................................................ 514/475

(58) Field of Classification Search
None
See application file for complete search history.

(56) References Cited

U.S. PATENT DOCUMENTS

| | | | | |
|---|---|---|---|---|
| 2,779,721 | A * | 1/1957 | Houtman, Jr. et al. | 549/541 |
| 5,250,208 | A * | 10/1993 | Merchant et al. | 252/67 |
| 5,516,951 | A * | 5/1996 | Aoyama | 570/175 |
| 5,618,902 | A * | 4/1997 | Wengrovius et al. | 528/10 |
| 6,843,934 | B2 * | 1/2005 | Bement et al. | 252/182.24 |
| 7,438,825 | B1 * | 10/2008 | Chen et al. | 252/68 |
| 8,066,901 | B1 * | 11/2011 | Hulse et al. | 252/67 |
| 2005/0033095 | A1 * | 2/2005 | Nappa et al. | 568/674 |
| 2010/0078585 | A1 | 4/2010 | Robin | |
| 2010/0163776 | A1 | 7/2010 | Robin | |
| 2010/0243943 | A1 | 9/2010 | Robin | |

FOREIGN PATENT DOCUMENTS

| | | |
|---|---|---|
| WO | 2008/121776 A1 | 10/2008 |
| WO | 2008/154612 A1 | 12/2008 |
| WO | 2009085857 A2 | 7/2009 |
| WO | 2009155490 A1 | 12/2009 |

OTHER PUBLICATIONS

PCT Search Report, dated Aug. 18, 2011. PCT/US10/60404, Filed Jul. 14, 2011.

* cited by examiner

*Primary Examiner* — Anna Pagonakis
*Assistant Examiner* — Jared D Barsky
(74) *Attorney, Agent, or Firm* — Colleen D. Szuch

(57) ABSTRACT

This invention relates to azeotrope-like compositions, methods and systems having utility in numerous applications, and in particular, uses for azeotrope-like compositions comprising effective amounts of the compound cis-1,1,1,4,4,4-hexafluoro-2-butene (Z-HFO-1336mzzm), which has the following structure:

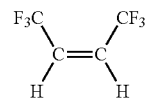

and another material selected from the group consisting of water, fluoroketones, alcohols, hydrochlorofluoroolefins, and combinations of two or more thereof. These compositions may be used in a wide variety of applications such as, blowing agents, refrigerants, heating agents, power cycle agents, cleaning agents, aerosol propellants, sterilization agents, lubricants, flavor and fragrance extractants, flammability reducing agents, and flame suppression agents.

4 Claims, 1 Drawing Sheet

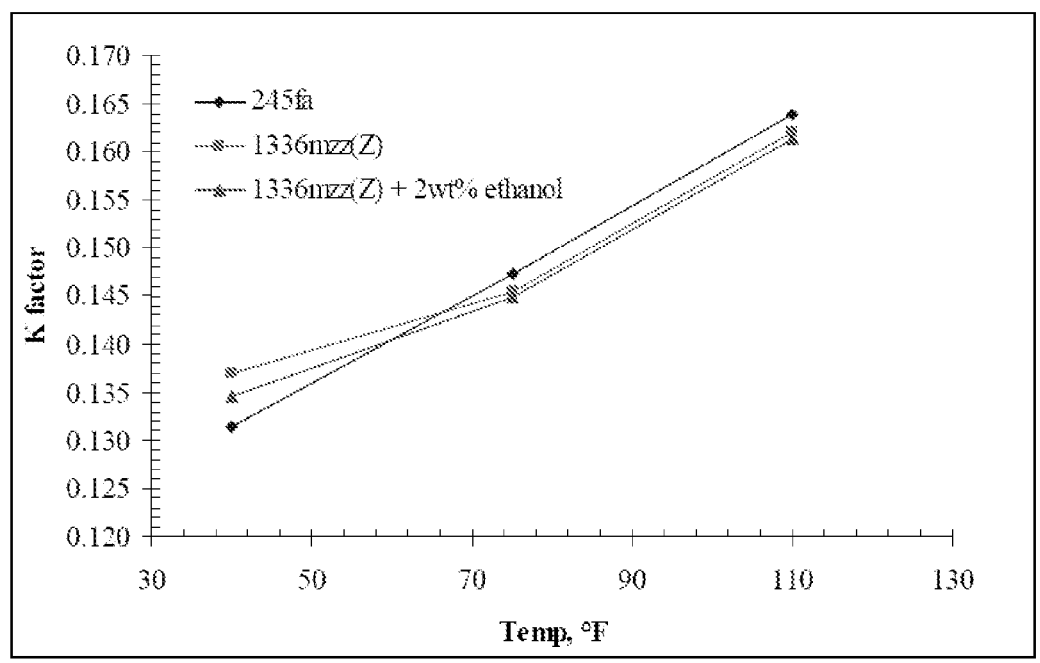
k factors of polyurethane foams

AZEOTROPE-LIKE COMPOSITIONS OF CIS-1,1,1,4,4,4-HEXAFLUORO-2-BUTENE

CROSS-REFERENCE TO RELATED APPLICATION

This application claims benefit of U.S. Provisional Patent Application Ser. No. 61/287,041 filed Dec. 16, 2009, the disclosure of which is hereby incorporated herein by reference.

FIELD OF THE INVENTION

This invention relates to azeotrope-like compositions, methods and systems having utility in numerous applications, and in particular, uses for azeotrope-like compositions comprising, or consisting essentially of, effective amounts of the compound cis-1,1,1,4,4,4-hexafluoro-2-butene (Z-HFO-1336mzzm), which has the following structure:

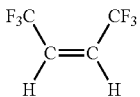

and another material selected from the group consisting of water, fluoroketones, alcohols, hydrochlorofluoroolefins, and combinations of two or more thereof.

BACKGROUND OF THE INVENTION

The azeotrope-like compositions of the present invention are part of a continued search for the next generation of low global warming potential materials. Such materials must have low environmental impact, as measured by ultra-low global warming potential and near zero ozone depletion potential.

The azeotrope-like compositions of the present invention may be used in a wide variety of applications such as blowing agents, refrigerants, heating agents, power cycle agents, cleaning agents, aerosol propellants, sterilization agents, lubricants, flavor and fragrance extractants, flammability reducing agents, and flame suppression agents, to name a few preferred uses.

SUMMARY OF THE INVENTION

Applicants have developed several azeotrope-like compositions which include as an essential component Z-HFO-1336mzzm. In certain embodiments, the other part of the azeotrope-like composition is at least one C1 to C12 alcohol compound. In other embodiments, the other part of the azeotrope-like composition is water. In other embodiments, the other part of the azeotrope-like composition is a fluoroketone compound. In other embodiments, the other part of the azeotrope-like composition is a hydrochlorofluoroolefin compound.

According to certain embodiments, the present invention provides azeotrope-like compositions comprising, or preferably consisting essentially of, from greater than zero to about 99 wt % of the compound Z-HFO-1336mzzm and from about 1 wt % to less than 100 wt % of an alcohol, and combinations of two or more thereof. Preferred alcohols are the C1 to C12 alcohols. Especially preferred are methanol and ethanol.

It should be noted that it would be common and expected for a product designated as Z-HFO-1336mzzm to include a minor percentage, for example about 0.5 wt % up to about 5 wt % of other components, including particularly E-HFO-1336mzzm. When used herein, the term "consisting essentially of Z-HFO-1336mzzm" is intended to generally include such compositions. The terms "consist of" and "consisting of" as used herein, do not include such other components. All of the embodiments of the invention described herein may, if desired, be obtained in a substantially purified form, such that these embodiments preferably consist of only the actual components designated, other than minor (e.g., ppm) impurities.

The present invention preferably provides azeotrope and azeotrope-like compositions comprising, or preferably consisting essentially of, Z-HFO-1336mzzm/ethanol or Z-HFO-1336mzzm/methanol. Preferably, the azeotrope-like compositions of the present invention comprise, or more preferably consist essentially of, effective amounts of Z-HFO-1336mzzm and ethanol or Z-HFO-1336mzzm and methanol. The term effective amount, as used herein, refers to the amount of each component which upon combination with the other component or components, results in the formation of the present azeotrope-like compositions.

In certain embodiments the azeotrope-like composition comprises, or preferably consists essentially of, from about 75 wt % to less than 100 wt % of Z-HFO-1336mzzm and from greater than zero to about 25 wt % of an alcohol, and combinations of two or more thereof.

In other embodiments, the azeotrope-like composition comprises, or preferably consists essentially of, from about 85 wt % to less than 100 wt % of Z-HFO-1336mzzm and from greater than zero to about 15 wt % of an alcohol, and combinations of two or more thereof.

Another embodiment of the present invention is directed to azeotrope-like compositions comprising from greater than zero to about 99 wt % of the compound water and from about 1 wt % to less than 100 wt % of Z-HFO-1336mzzm.

In certain embodiments the azeotrope-like composition comprises, or preferably consists essentially of, from greater than zero to about 50 wt % of water and from about 50 wt % to less than 100 wt % of Z-HFO-1336mzzm.

In other embodiments, the azeotrope-like composition comprises, or preferably consists essentially of, from greater than zero to about 10 wt % of water and from about 90 wt % to less than 100 wt % of Z-HFO-1336mzzm.

One embodiment of the invention is a blowing agent comprising, or consisting essentially of, one or more of the azeotrope-like composition of the present invention.

Another embodiment of the invention is a method of forming a foam comprising adding to a foamable composition a blowing agent comprising, or consisting essentially of one or more of the azeotrope-like compositions of the present invention. The blowing agent may further comprise a premix of a polyol and the blowing agent, wherein the blowing agent comprises an azeotrope-like composition of the present invention.

Yet another embodiment of the invention is a closed cell foam prepared by foaming a foamable composition in the presence of a blowing agent comprising, or consisting essentially of, one or more of the azeotrope-like compositions of the present invention. Preferably, the closed cell foam is formed from a foamable composition that further comprises polyurethane, polyisocyanurate, polystyrene, polyethylene, and mixtures thereof.

One embodiment of the invention is a refrigerant composition comprising, or consisting essentially of, one or more of the azeotrope-like compositions of the present invention. Another embodiment of the invention is a refrigeration system comprising a refrigerant composition of the present invention. Yet another embodiment of the invention is a method for cooling an article which comprises evaporating a refrigerant composition of the invention in the vicinity of the article to be cooled.

Another embodiment of the invention is a method for heating an article which comprises condensing a refrigerant composition comprising, or consisting essentially of, one or more of the azeotrope-like compositions of the present invention in the vicinity of the article to be heated.

One embodiment of the invention is a sprayable composition comprising a material to be sprayed and a propellant comprising, or consisting essentially of, one or more of the azeotrope-like compositions of the present invention.

Yet another embodiment of the invention is a method of reducing the flammability of a fluid comprising adding one or more of the azeotrope-like compositions of the present invention to said fluid.

Another embodiment of the invention is a method of suppressing a flame comprising contacting said flame with a fluid comprising one or more of the azeotrope-like compositions of the present invention. Optionally, this fluid may further include one or more fluoroketone compounds. One preferred fluoroketone compound is dodecafluoro-2-methylpentan-3-one. One source for this compound is the 3M Company under the brand name Novec 1230.

Yet another embodiment of the invention is a method of cleaning and/or sterilizing an article, said method comprising contacting said article to be cleaned or sterilized with a composition comprising, or consisting essentially of, one or more of the azeotrope-like compositions of the present invention. Optionally, the composition may further include ethylene oxide.

Azeotrope-Like

The term azeotrope-like refers to compositions that behave like azeotropic mixtures, that is, the composition of the vapor formed during boiling or evaporation is identical, or substantially identical, to the original liquid composition. Thus, with boiling or evaporation, the liquid composition changes, if at all, only to a minimal or negligible extent. This is to be contrasted with non-azeotrope-like compositions in which, during boiling or evaporation, the liquid composition changes to a substantial degree.

The term azeotrope-like is thus intended in its broad sense to include both compositions that are strictly azeotropic and compositions that behave like azeotropic mixtures. From fundamental principles, the thermodynamic state of a fluid is defined by pressure, temperature, liquid composition, and vapor composition. An azeotropic mixture is a system of two or more components in which the liquid composition and vapor composition are equal at the state pressure and temperature. In practice, this means that the components of an azeotropic mixture are constant boiling and cannot be separated during a phase change.

The term "azeotrope-like" especially refers to a combination of the compound Z-HFO-1336mzzm with one or more compounds that behave substantially like a single compound in so far as the vapor in substantial equilibrium with the liquid has substantially the same concentration of components present in the liquid.

Azeotropes-like compositions according to the present invention include absolute azeotropes (compositions in which azeotropic conditions are satisfied, at a particular pressure, over all values of temperature (up to the critical stage)) or limited azeotropes (compositions in which azeotropic conditions are satisfied only in a certain temperature range at a particular pressure). Azeotropes-like compositions according to the present invention also include homo-azeotropes, wherein, at a given pressure, the composition exists in a single liquid phase, or hetero-azeotropes, wherein, at a given pressure, the composition exists as two or more liquid phases. Moreover, azeotrope-like compositions according to the present invention can be binary, ternary, quaternary, or quinary azeotropes depending on whether the composition is composed of 2, 3, 4, or 5 compounds, respectively (or more).

The azeotrope-like compositions of the invention may include additional components that do not form new azeotrope-like systems, or additional components that are not in the first distillation cut. The first distillation cut is the first cut taken after the distillation column displays steady state operation under total reflux conditions. One way to determine whether the addition of a component forms a new azeotrope-like system so as to be outside of this invention is to distill a sample of the composition with the component under conditions that would be expected to separate a non-azeotropic mixture into its separate components. If the mixture containing the additional component is non-azeotrope-like, the additional component will fractionate from the azeotrope-like components. If the mixture is azeotrope-like, some finite amount of a first distillation cut will be obtained that contains all of the mixture components that is constant boiling or behaves as a single substance.

It follows from this that another characteristic of azeotrope-like compositions is that there is a range of compositions containing the same components in varying proportions that are azeotrope-like or constant boiling. As used herein, "constant boiling" means that the boiling point of the composition does not vary by no more than about $\pm 2°$ C., preferably by no more than about $\pm 1°$ C., more preferably by no more than about $\pm 0.5°$ C., and most preferably by no more than about $\pm 0.2°$ C. over a change of the azeotrope-like composition. All such compositions are intended to be covered by the terms "azeotrope-like" and "constant boiling." As an example, it is well known that at differing pressures, the composition of a given azeotrope will vary at least slightly, as does the boiling point of the composition.

As described above, the azeotrope-like compositions of the invention are constant boiling or essentially constant boiling. In other words, for these azeotrope-like compositions, the composition of the vapor formed during boiling or evaporation is identical, or substantially identical, to the original liquid composition. Thus, with boiling or evaporation, the liquid composition changes, if at all, only to a minimal or negligible extent. This is to be contrasted with non-azeotrope-like compositions in which, during boiling or evaporation, the liquid composition changes to a substantial degree.

Thus, an azeotrope-like composition of component A and component B represents a unique type of relationship, but with a variable composition depending on temperature and/or pressure. It follows that, for azeotrope-like compositions, there is a range of compositions containing the same components in varying proportions that are azeotrope-like. All such compositions are intended to be covered by the term azeotrope-like as used herein.

The preferred azeotrope-like compositions of the present invention are environmentally acceptable and do not to contribute to the depletion of the earth's stratospheric ozone layer. The compounds and compositions of the present invention have no substantial ozone depletion potential (ODP), preferably an ODP of not greater than about 0.5 and even more preferably an ODP of not greater than about 0.25, most preferably an ODP of not greater than about 0.1; and/or a global warming potential (GWP) of not greater than about 150, and even more preferably, a GWP of not greater than about 50. Preferably, both criteria are met by the compositions.

As used herein, ODP is defined in the "Scientific Assessment of Ozone Depletion, 2002," a report of the World Meteorological association, incorporated here by reference.

As used herein, GWP is defined relative to that of carbon dioxide and over a 100 year time horizon, and defined in the same reference as for the ODP mentioned above.

In one preferred embodiment, the present invention provides azeotrope-like compositions comprising, or preferably consisting essentially of, Z-HFO-1336mzzm and ethanol. Another preferred embodiment of the present invention provides the azeotrope-like compositions comprising, or preferably consisting essentially of, Z-HFO-1336mzzm and methanol. Other alcohols can likewise be employed, such as propanol, butanol, pentanol, hexanol, octanol, nonanal, decanol, and the like.

BRIEF DESCRIPTION OF THE DRAWING

FIG. 1 illustrates k factors of polyurethane foams.

DETAILED DESCRIPTION OF PREFERRED EMBODIMENTS

In the azeotrope-like compositions of the present invention, the amount of the Z-HFO-1336mzzm may vary widely, including in all cases constituting the balance of the composition after all other components in composition are accounted for.

As described above, methanol and ethanol are preferred alcohols employed in preferred azeotrope-like compositions of the present invention. These embodiments preferably provide azeotrope-like compositions comprising, and preferably consisting essentially of, from greater than zero to about 50 parts by weight ethanol, and from about 50 to less than 100 parts by weight of Z-HFO-1336mzzm, more preferably from greater than zero to about 20 parts by weight ethanol, and from about 80 to less than 100 parts by weight of Z-HFO-1336mzzm, and even more preferably from greater than zero to about 10 parts by weight ethanol, and from about 90 to less than 100 parts by weight of Z-HFO-1336mzzm. Preferred ethanol based azeotrope-like compositions of the present invention are characterized by a boiling point of about 31.3° C., preferably ±2° C., more preferably ±1° C. at 14.3 psia.

These embodiments preferably provide azeotrope-like compositions comprising, and preferably consisting essentially of, from about 1 to about 50 parts by weight methanol, and from about 50 to about 99 parts by weight of Z-HFO-1336mzzm, more preferably from about 1 to about 70 parts by weight methanol, and from about 30 to about 99 parts by weight of Z-HFO-1336mzzm, and even more preferably from about 1 to about 85 parts by weight methanol, and from about 15 to about 99 parts by weight of Z-HFO-1336mzzm. Preferred compositions of the present invention are characterized by a boiling point of about 29.7° C., preferably ±2° C., more preferably ±1° C. at 14.3 psia.

Additional components may be added to tailor the properties of the azeotrope-like compositions of the invention as needed. By way of example, oil solubility aids may be added in the case in which the azeotrope-like compositions of the invention are used as refrigerants. Stabilizers and other materials may also be added to enhance the properties of the azeotrope-like compositions of the invention.

The ethanol or methanol can be removed from the azeotrope using an extractant such as water. Due to each alcohol's high solubility in water the alcohol will be removed to the aqueous phase and the Z-HFO-1336mzzm will phase separate from the aqueous phase leaving behind a purified Z-HFO-1336mzzm. The alcohol can then be extracted from the water using common drying techniques such as a molecular sieve.

Other embodiments preferably provide azeotrope-like compositions comprising, and preferably consisting essentially of, from about 1 to about 50 parts by weight water, and from about 50 to about 99 parts by weight of Z-HFO-1336mzzm, more preferably from about 10 to about 40 parts by weight water, and from about 60 to about 90 parts by weight of Z-HFO-1336mzzm, and even more preferably from about 15 to about 35 parts by weight water, and from about 65 to about 85 parts by weight of Z-HFO-1336mzzm. Preferred compositions of the present invention are characterized by a boiling point of about 31.4° C., preferably ±2° C., more preferably ±1° C. at 14.5 psia.

Other embodiments preferably provide azeotrope-like compositions comprising, and preferably consisting essentially of, from about 1 to about 50 parts by weight of the fluoroketone dodecafluoro-2-methylpentan-3-one, and from about 50 to about 99 parts by weight of Z-HFO-1336mzzm, more preferably from about 5 to about 45 parts by weight Novec 1230, and from about 55 to about 95 parts by weight of Z-HFO-1336mzzm, and even more preferably from about 10 to about 30 parts by weight of the fluoroketone, and from about 70 to about 90 parts by weight of Z-HFO-1336mzzm. Preferred compositions of the present invention are characterized by a boiling point of about 32.0° C., preferably ±2° C., more preferably ±1° C. at 14.5 psia.

Compositions according to the present invention, including the preferred azeotrope-like compositions, may include one or more components, such as additives, which may not form new azeotrope-like compositions. Known additives may be used in the present compositions in order to tailor the composition for a particular use Inhibitors may also be added to the present compositions to inhibit decomposition, react with undesirable decomposition products, and/or prevent the corrosion of metal surfaces. Typically, up to about 2 percent of an inhibitor based on the total weight of the azeotrope-like composition may be used.

Azeotrope Additives

The azeotrope-like compositions of the present invention may further include any of a variety of optional additives including stabilizers, metal passivators, corrosion inhibitors, and the like.

According to certain embodiments, the azeotrope-like compositions of the present invention further comprise a stabilizer. Any of a variety of compounds suitable for stabilizing an azeotrope-like composition of the present invention may be used. Examples of certain preferred stabilizers include stabilizer compositions comprising at least one phenol composition and at least one epoxide selected from the group consisting of aromatic epoxides, alkyl epoxides, alkenyl epoxides, and combinations of two or more thereof. The stabilizer mixture may further be comprised of nitromethane, 1,2-butylene oxide and 1,3-dioxolane or 1,4-dioxane. It has also been found that various terpene hydrocarbons and terpene alcohols as well as mineral spirits, glycol ethers, alcohols, and ketones can be used in conjunction with the above identified stabilizer mixture.

Any of a variety of phenol compounds is suitable for use in the present compositions. While applicants do not wish to be bound by or to any theory of operation, it is believed that the phenols act as radical scavengers in the azeotrope-like compositions and thereby tend to increase the stability of such compositions. As used herein the term phenol compound refers generally to any substituted or unsubstituted phenol. Examples of suitable phenol compounds include phenols comprising one or more substituted or unsubstituted cyclic, straight-chain, or branched aliphatic substituent group, such as, alkylated monophenols including: 2,6-di-tert-butyl-4-methylphenol; 2,6-di-tert-butyl-4-ethylphenol; 2,4-dimethyl-6-tert-butylphenol; tocopherol; and the like, hydroquinone and alkylated hydroquinones including: t-butyl hydroquinone; other derivatives of hydroquinone; and the like, hydroxylated thiodiphenyl ethers including: 4,4'-thiobis(2-methyl-6-tert-butylphenol); 4,4'-thiobis(3-methyl-6-tert-butylphenol); 2,2'-thiobis(4-methyl-6-tert-butylphenol); and the like, alkylidene-bisphenols including: 4,4'-methylenebis(2,6-di-tert-butylphenol); 4,4'-bis(2,6-di-tert-butylphenol; derivatives of 2,2- or 4,4-biphenyldiols; 2,2'-methylenebis(4-ethyl-6-tert-butylphenol); 2,2'-methylenebis(4-methyl-6-tert-butylphenol); 4,4,-butylidenebis(3-methyl-6-tert-butylphenol); 4,4,-isopropylidenebis(2,6-di-tert-butylphenol); 2,2'-methylenebis(4-methyl-6-nonylphenol); 2,2'-isobutylidenebis(4,6-dimethylphenol); 2,2'-methylenebis(4-methyl-6-cyclohexylphenol), 2,2- or 4,4-biphenyldiols including 2,2'-methylenebis(4-ethyl-6-tertbutylphenol), butylated hydroxy toluene (BHT), bisphenols comprising heteroatoms including: 2,6-di-tert-.alpha.-dimethylamino-p-cresol; 4,4-thiobis(6-tert-butyl-m-cresol); and the like; acylaminophenols; 2,6-di-tert-butyl-4(N,N'-dimethylaminomethylphenol); sulfides including: bis(3-methyl-4-hydroxy-5-tert-butylbenzyl)sulfide; bis(3,5-di-tert-butyl-4-hydroxybenzyl)sulfide; and the like; as well as, phenolic UV absorb and light stabilizers.

Certain preferred phenols include alkylated monophenols such as tocopherol, BHT, hydroquinones, and the like. Certain particularly preferred phenols include tocopherol, and the like. Most phenols are commercially available. A single phenol compound and/or mixtures of two or more phenols may be used in the present compositions. Any of a variety of epoxides will be suitable for use in the azeotrope-like compositions of the present invention. While applicants do not wish to be bound by or to any theory of operation, it is believed that the epoxides of the present invention act as acid scavengers in the azeotrope-like compositions and thereby tend to increase the stability of such compositions. A single aromatic epoxide and/or mixtures of two or more aromatic epoxides may be used in the present compositions.

In certain other preferred embodiments, the alkyl epoxide for use as an acid scavenger in the present composition comprises polypropylene glycol diglycidyl ether. Examples of polypropylene glycol diglycidyl ether suitable for use in the present invention include the ether available commercially from SACHEM, Europe.

In addition, in certain embodiments, the epoxide for use in the present invention comprises combinations of two or more aromatic, alkyl, and/or alkenyl substituents. Such epoxides are referred to generally as "multisubstituted epoxides." According to certain preferred embodiments, the stabilizer for use in the present invention comprises a combination of at least one phenol compound and at least one aromatic, alkyl, or alkenyl epoxide. Examples of suitable combinations include stabilizers comprising: tocopherol and allyl glycidyl ether, BHT and glycidyl butyl ether, and the like. Certain particularly preferred combinations include stabilizers comprising: tocopherol and allyl glycidyl ether, and the like.

Any suitable relative amount of the at least one phenol compound and the at least one aromatic, alkyl, or alkenyl epoxide may be used in the preferred stabilizers. For example, the weight ratio of phenol compound(s) to aromatic or fluorinated alkyl epoxide(s) can be varied from about 1:99 to about 99:1. In certain preferred embodiments, the weight ratios of phenol compound(s) to aromatic, alkyl, alkenyl, multisubstituted, or fluorinated alkyl epoxide(s) is from about 30 to about 1, more preferably from about 7 to about 1, more preferably from about 2 to about 1, and even more preferably about 1:1.

AZEOTROPE EXAMPLES

Example 1

A sample of 69.4 wt % Z-HFO-1336mzzm, 3.1 wt % ethanol, 7.6 wt % lights and remainder heavies was charged into a Monel distillation column. The distillation column is a spinning band column that operated at atmospheric pressure. The condenser was cooled using a thermostated propylene glycol water solution.

The distillation column was initially operated at full reflux and allowed to reach temperature and pressure equilibrium at each of the desired conditions. Once the column had achieved equilibrium a vapor sample was taken from the overhead of the distillation column. The overhead of the column was periodically sampled as the distillate was collected. After the lights had been removed from the distillation column a sample was taken. The sample showed 2.0 wt % ethanol in the Z-HFO-1336mzzm. The ethanol persisted through the Z-HFO-1336mzzm cut indicating that an azeotrope had been formed.

Example 2

An ebulliometer was used to measure the azeotrope of Z-HFO-1336mzzm and ethanol. The ebulliometer consist of a vacuum insulated glass vessel which is sealed at the bottom and open to the atmosphere at the top. The top or condenser portion of the ebulliometer is surrounded by dry ice to ensure that all vapors are condensed and allowed to flow back into the ebulliometer. Initially Z-HFO-1336mzzm was charged into the ebulliometer and ethanol was metered in.

Table 1 shows a minimum in temperature which indicates that an azeotrope has been formed. The bubble point temperature of the mixture remains constant indicating that this mixture is azeotrope-like over a large composition range.

TABLE 1

Ebulliometer measurements of Z-HFO-1336mzzm and Ethanol at 14.3 psia

| Z-HFO-1336mzzm, wt % | Ethanol, wt % | Temp, ° C. |
|---|---|---|
| 100.00 | 0.00 | 31.6 |
| 99.59 | 0.41 | 31.3 |
| 97.97 | 2.03 | 31.2 |
| 95.65 | 4.35 | 31.1 |
| 93.43 | 6.57 | 31.1 |
| 89.95 | 10.05 | 31.1 |
| 84.30 | 15.70 | 31.2 |
| 79.32 | 20.68 | 31.3 |
| 74.90 | 25.10 | 31.3 |
| 70.53 | 29.47 | 31.3 |
| 66.64 | 33.36 | 31.4 |
| 63.15 | 36.85 | 31.4 |

Example 2

An ebulliometer as in Example 2 was used to measure the azeotrope of Z-HFO-1336mzzm and methanol. Initially Z-HFO-1336mzzm was charged into the ebulliometer and methanol was metered in.

Table 2 shows a minimum in temperature which indicates that an azeotrope has been formed. The bubble point temperature of the mixture remains constant indicating that this mixture is azeotrope-like over a large composition range.

TABLE 2

Ebulliometer measurements of Z-HFO-1336mzzm and Methanol at 14.3 psia

| Z-HFO-1336mzzm, wt % | Methanol, wt % | Temp, ° C. |
|---|---|---|
| 100.00 | 0.00 | 32.02 |
| 99.59 | 0.41 | 30.81 |
| 98.78 | 1.22 | 29.92 |
| 97.20 | 2.80 | 29.68 |
| 94.19 | 5.81 | 29.66 |
| 91.35 | 8.65 | 29.66 |
| 86.17 | 13.83 | 29.78 |
| 81.55 | 18.45 | 29.80 |
| 77.39 | 22.61 | 29.90 |
| 73.19 | 26.81 | 29.94 |
| 69.43 | 30.57 | 29.99 |
| 66.03 | 33.97 | 30.14 |
| 62.96 | 37.04 | 30.24 |
| 60.15 | 39.85 | 30.44 |

Example 3

An ebulliometer as used in Example 2 was used to measure the azeotrope of Z-HFO-1336mzzm and dodecafluoro-2-methylpentan-3-one (Novec 1230). Initially Z-HFO-1336mzzm was charged into the ebulliometer and the fluoroketone Novec 1230 (3M Company) was metered in.

Table 3 shows a minimum in temperature which indicates that an azeotrope has been formed. The bubble point temperature of the mixture remains constant indicating that this mixture is azeotrope-like over a large composition range.

TABLE 3

Ebulliometer measurements of Z-HFO-1336mzzm and Novec 1230 at 14.5 psia

| Z-HFO-1336mzzm, wt % | NOVEC 1230, wt % | Temp, ° C. |
|---|---|---|
| 100.00 | 0.00 | 32.7 |
| 99.25 | 0.75 | 32.6 |
| 97.77 | 2.23 | 32.4 |
| 94.95 | 5.05 | 32.2 |
| 89.78 | 10.22 | 32.0 |
| 82.99 | 17.01 | 32.0 |
| 75.39 | 24.61 | 32.1 |
| 69.06 | 30.94 | 32.1 |
| 63.72 | 36.28 | 32.2 |
| 58.61 | 41.39 | 32.4 |
| 54.27 | 45.73 | 32.5 |
| 50.52 | 49.48 | 32.7 |
| 47.26 | 52.74 | 32.8 |
| 44.39 | 55.61 | 33.0 |

Example 4

The compound E-HCFO-1233zd (trans-1,1,1-trifluoro-3-chloropropene) has also been found to form an azeotrope-like composition with Z-HFO-1336mzzm. As shown below in Table 4, it has been found that the azeotrope-like properties of this composition continue up to about 10 wt % Z-HFO-1336mzzm. These compositions are especially useful for spray foam applications.

TABLE 4

Ebulliometer measurements of Z-HFO-1336mzzm and E-HCFO-1233zd at 14.5 psia
Ebulliometer study of 1233zd (E)/1336mzzm (Z)

| wt % 1233zd (E) | wt % 1336mzzm (Z) | Temp. (° C.) |
|---|---|---|
| 100.00 | 0.00 | 17.70 |
| 99.60 | 0.40 | 17.70 |
| 98.82 | 1.18 | 17.73 |
| 97.28 | 2.72 | 17.75 |
| 95.79 | 4.21 | 17.81 |
| 92.95 | 7.05 | 17.89 |
| 87.74 | 12.26 | 18.02 |
| 83.64 | 16.36 | 18.18 |
| 79.39 | 20.61 | 18.37 |
| 75.56 | 24.44 | 18.56 |
| 72.08 | 27.92 | 18.76 |
| 68.91 | 31.09 | 18.98 |
| 65.66 | 34.34 | 19.18 |
| 62.70 | 37.30 | 19.36 |
| 59.99 | 40.01 | 19.54 |
| 57.88 | 42.12 | 19.58 |
| 42.93 | 57.07 | 20.90 |
| 35.54 | 64.46 | 21.81 |
| 25.80 | 74.20 | 23.22 |
| 15.66 | 84.34 | 25.13 |
| 4.67 | 95.33 | 30.44 |
| 0.18 | 99.82 | 32.79 |
| 0.00 | 100.00 | 32.81 |

Example 5

An ebulliometer as in Example 2 was used to measure the azeotrope of Z-HFO-1336mzzm and water. Initially Z-HFO-1336mzzm was charged into the ebulliometer and water was metered in. Table 5 shows a minimum in temperature which indicates that an azeotrope has been formed. The bubble point temperature of the mixture remains constant indicating that this mixture is azeotrope-like over a large composition range.

TABLE 5

Ebulliometer measurements of Z-HFO-1336mzzm and water at 14.5 psia

| Z-HFO-1336mzzm, wt % | Water, wt % | Temp, ° C. |
|---|---|---|
| 100.0 | 0.0 | 32.4 |
| 99.4 | 0.6 | 32.3 |
| 98.2 | 1.8 | 32.0 |
| 97.1 | 2.9 | 31.8 |
| 96.0 | 4.0 | 31.7 |
| 93.9 | 6.1 | 31.5 |
| 89.8 | 10.2 | 31.4 |
| 82.8 | 17.2 | 31.4 |
| 76.7 | 23.3 | 31.4 |
| 71.5 | 28.5 | 31.4 |
| 66.9 | 33.1 | 31.4 |
| 62.9 | 37.1 | 31.4 |
| 59.4 | 40.6 | 31.4 |

Uses of the Azeotrope-Like Compositions

As described above, any of the azeotrope-like compositions of the invention may be used in a wide variety of applications as substitutes for CFCs and for compositions containing less desirable HCFCs.

Specifically, the azeotrope-like compositions comprising, or consisting essentially of, effective amounts of Z-HFO-1336mzzm and another material selected from the group consisting of water, fluoroketones, alcohols, hydrochlorofluoroolefins, and combinations of two or more thereof, are useful as blowing agents, refrigerants, heating agents, power cycle agents, cleaning agents, aerosol propellants, sterilization agents, lubricants, flavor and fragrance extractants, flammability reducing agents, and flame suppression agents, to name a few preferred uses. Each of these uses will be discussed in greater detail below.

Blowing Agents

One embodiment of the present invention relates to a blowing agent comprising one or more of the azeotrope-like compositions of the invention. In other embodiments, the invention provides foamable compositions, and preferably polyurethane and polyisocyanurate foam compositions, and methods of preparing foams. In such foam embodiments, one or more of the azeotrope-like compositions, are included as a blowing agent in a foamable composition, which composition preferably includes one or more additional components capable of reacting and foaming under the proper conditions to form a foam or cellular structure, as is well known in the art.

The present methods preferably comprise providing such a foamable composition and reacting it under conditions effective to obtain a foam, and preferably a closed cell foam. The invention also relates to foam, and preferably closed cell foam, prepared from a polymer foam formulation containing a blowing agent comprising an azeotrope-like composition of the invention.

In certain embodiments, one or more of the following HFC isomers are preferred for use as co-blowing agents in the azeotrope-like compositions of the present invention:
1,1,1,2,2-pentafluoroethane (HFC-125)
1,1,2,2-tetrafluoroethane (HFC-134)
1,1,1,2-tetrafluoroethane (HFC-134a)
1,1-difluoroethane (HFC-152a)
1,1,1,2,3,3,3-heptafluoropropane (HFC-227ea)
1,1,1,3,3,3-hexafluoropropane (HFC-236fa)
1,1,1,3,3-pentafluoropropane (HFC-245fa) and
1,1,1,3,3-pentafluorobutane (HFC-365mfc).

The relative amount of any of the above noted additional co-blowing agents, as well as any additional components which may be included in the present azeotrope-like compositions, can vary widely within the general broad scope of the present invention according to the particular application for the composition, and all such relative amounts are considered to be within the scope hereof Foams The present invention also relates to all foams, including but not limited to closed cell foam, open cell foam, rigid foam, flexible foam, integral skin and the like, prepared from a polymer foam formulation containing a blowing agent comprising an azeotrope-like composition comprising, or consisting essentially of, Z-HFO-1336mzzm and one or more alcohols, preferably methanol or ethanol. Applicants have found that one advantage of the foams, and particularly thermoset foams such as polyurethane foams, in accordance with the present invention is the ability to achieve, preferably in connection with thermoset foam embodiments, exceptional thermal performance, such as can be measured by the k-factor or lambda, particularly and preferably under low temperature conditions, as shown in FIG. 1.

Although it is contemplated that the present foams, particularly thermoset foams of the present invention, may be used in a wide variety of applications, in certain preferred embodiments the present invention comprises appliance foams in accordance with the present invention, including refrigerator foams, freezer foams, refrigerator/freezer foams, panel foams, and other cold or cryogenic manufacturing applications.

The foams prepared in accordance with the present invention, in certain preferred embodiments, provide one or more exceptional features, characteristics and/or properties, including: thermal insulation efficiency (particularly for thermoset foams), dimensional stability, compressive strength, aging of thermal insulation properties, all in addition to the low ozone depletion potential and low global warming potential associated with many of the preferred blowing agents of the present invention.

In certain highly preferred embodiments, the present invention provides thermoset foam, including such foam formed into foam articles, which exhibit improved thermal conductivity relative to foams made using the same blowing agent (or a commonly used blowing agent HFC-245fa) in the same amount but without the azeotrope-like composition of the present invention.

Any of the methods well known in the art, such as those described in Polyurethanes Chemistry and Technology, Volumes I and II, Saunders and Frisch, 1962, John Wiley and Sons, New York, N.Y., which is incorporated herein by reference, may be used or adapted for use in accordance with the foam embodiments of the present invention. In general, such preferred methods comprise preparing polyurethane or polyisocyanurate foams by combining an isocyanate, a polyol or mixture of polyols, a blowing agent or mixture of blowing agents comprising one or more of the present compositions, and other materials such as catalyst, as well as surfactants, and optionally, flame retardants, colorants, or other additives.

It is convenient in many applications to provide the components for polyurethane or polyisocyanurate foams in pre-blended formulations. Most typically, the foam formulation is pre-blended into two components. The isocyanate and optionally certain surfactants and blowing agents comprise the first component, commonly referred to as the A component. The polyol or polyol mixture, surfactant, catalysts, blowing agents, flame retardant, and other isocyanate reactive components comprise the second component, commonly referred to as the B component. Accordingly, polyurethane or polyisocyanurate foams are readily prepared by bringing together the A and B side components either by hand mix for small preparations and, preferably, machine mix techniques to form blocks, slabs, laminates, pour-in-place panels and other items, spray applied foams, froths, and the like. Optionally, other ingredients such as fire retardants, colorants, auxiliary blowing agents, and even other polyols can be added as a third stream to the mix head or reaction site. Most conveniently, however, they are all incorporated into one B-component as described above.

It is also possible to produce thermoplastic foams using the azeotrope-like compositions of the invention. For example, conventional foam polyurethanes and isocyanurate formulations may be combined with the azeotrope-like compositions in a conventional manner to produce rigid foams.

Dispersing agents, cell stabilizers, and surfactants may also be incorporated into the blowing agent mixture. Surfactants, most notably silicone oils, are added to serve as cell stabilizers. Some representative materials are sold under the names of DC-193, B-8404, and L-5340 which are, generally, polysiloxane polyoxyalkylene block co-polymers such as those disclosed in U.S. Pat. Nos. 2,834,748, 2,917,480, and 2,846,458. Other optional additives for the blowing agent mixture may include flame retardants such as tri(2-chloroethyl)phosphate, tri(2-chloropropyl)phosphate, tri(2,3-dibromopropyl)-phosphate, tri(1,3-dichloropropyl)phosphate, diammonium phosphate, various halogenated aromatic compounds, antimony oxide, aluminum trihydrate, polyvinyl chloride, and the like.

In general, the amount of blowing agent present in the blended mixture used to form the foamable composition of the present invention is dictated by the desired foam densities of the final polyurethane or polyisocyanurate foams products. The polyurethane foams produced can vary in density from about 0.5 pound per cubic foot to about 40 pounds per cubic foot, preferably from about 1.0 to about 20.0 pounds per cubic foot, and most preferably from about 1.5 to about 6.0 pounds per cubic foot for rigid polyurethane foams and from about 1.0 to about 4.0 pounds per cubic foot for flexible foams. The density obtained is a function of several factors, including how much of the blowing agent, or blowing agent mixture, is present in the A and/or B components, or that is added at the time the foam is prepared.

Blowing Agent & Foam Example

This example demonstrates the performance of blowing agents comprising Z-HFO-1336mzzm and alcohols used in connection with the preparation of polyurethane foams. Three separate blowing agents were prepared for this example. The first blowing agent is HFC-245fa. The second blowing agent is Z-HFO-1336mzzm. The third blowing agent comprises an azeotrope-like composition comprising Z-HFO-1336mzzm in a concentration of approximately 98 weight percent of the total blowing agent, and ethanol in a concentration of approximately 2 weight percent of the total blowing agent.

In each system, the blowing agent was added in substantially the same molar concentration into the polyol blend. Foams were then formed using each blowing agent and the k-factors of the foams are measured. The formulation used is contained in the Table 6 below. The foams were prepared with a 3 second pour time and a 8 second mix time. The raw material temperatures were 50° F. polyol/70° F. MDI.

TABLE 6

Polyol Master Batch Composition

| Component | php |
|---|---|
| Manich polyether polyol, OH 470 | 80.00 |
| Aromatic polyester polyol | 70.00 |
| Diethylene glycol | 10.00 |
| Silicone surfactant | 2.00 |
| Dimethyl ethanol amine | 3.20 |
| Neutral chlorinated phosphate ester | 20.00 |
| Water | 2.00 |
| Total | 187.20 |
| Moles blowing agent | 0.698 |
| Index | 110 |

Table 7 below and FIG. 1 illustrate the k-factor performance of the three blowing agents.

TABLE 7 k Factors of Polyurethane Foams

| 245fa | | Z-HFO-1336mzzm | | Z-HFO-1336mzzm + 2 wt % ethanol | |
|---|---|---|---|---|---|
| Temp, °F. | k, BTU/hr ft² °F. | Temp, °F. | k, BTU/hr ft² °F. | Temp, °F. | k, BTU/hr ft² °F. |
| 40 | 0.132 | 40 | 0.137 | 40 | 0.135 |
| 75 | 0.147 | 75 | 0.146 | 75 | 0.145 |
| 110 | 0.164 | 110 | 0.162 | 110 | 0.161 |

One unexpected result illustrated by this example is the improved low temperature k factor of the 98 wt % Z-HFO-1336mzzm and 2 wt % ethanol blend over that of the neat Z-HFO-1336mzzm blowing agent.

Spray Foams

In a spray foam example, it was surprisingly found that there was a significant and unanticipated positive effect on the thermal conductivity of the foam by use of an azeotrope-like composition consisting essentially of 4 wt % of Z-HFO-1336mzzm and 96 wt % 1233zd(E). The foams prepared with this blowing agent composition aged slower across all temperature ranges and had better thermal conductivity properties than foams prepared with a blowing agent containing only 1233zd(E).

Methods and Systems

The azeotrope-like compositions of the invention are also useful in connection with numerous methods and systems, including as heat transfer fluids in methods and systems for transferring heat, such as refrigerants used in refrigeration, air conditioning and heat pump systems. The present azeotrope-like compositions are also advantageous for in use in systems and methods of generating aerosols, preferably comprising or consisting of the aerosol propellant in such systems and methods. Methods of forming foams and methods of extinguishing and suppressing fire are also included in certain aspects of the present invention. The present invention also provides in certain aspects methods of removing residue from articles in which the present azeotrope-like compositions are used as solvent compositions in such methods and systems.

Heat Transfer Methods

The preferred heat transfer methods generally comprise providing an azeotrope-like composition of the present invention and causing heat to be transferred to or from the composition by changing the phase of the composition. For example, the present methods provide cooling by absorbing heat from a fluid or article, preferably by evaporating the present refrigerant composition in the vicinity of the body or fluid to be cooled to produce vapor comprising the present composition.

Preferably the methods include the further step of compressing the refrigerant vapor, usually with a compressor or similar equipment to produce vapor of the present composition at a relatively elevated pressure. Generally, the step of compressing the vapor results in the addition of heat to the vapor, thus causing an increase in the temperature of the relatively high-pressure vapor. Preferably, the present methods include removing from this relatively high temperature, high pressure vapor at least a portion of the heat added by the evaporation and compression steps. The heat removal step preferably includes condensing the high temperature, high-pressure vapor while the vapor is in a relatively high-pressure condition to produce a relatively high-pressure liquid comprising a composition of the present invention. This relatively high-pressure liquid preferably then undergoes a nominally isoenthalpic reduction in pressure to produce a relatively low temperature, low-pressure liquid. In such embodiments, it is this reduced temperature refrigerant liquid which is then vaporized by heat transferred from the body or fluid to be cooled.

In another process embodiment of the invention, the azeotrope-like compositions of the invention may be used in a method for producing heating which comprises condensing a refrigerant composition comprising, or consisting essentially of, the azeotrope-like compositions of this invention, in the vicinity of a liquid or body to be heated. Such methods, as mentioned hereinbefore, frequently are reverse cycles to the refrigeration cycle described above.

Refrigerant Compositions

The azeotrope-like compositions of the present invention are adaptable for use in connection with automotive air conditioning systems and devices, commercial refrigeration systems and devices, chillers, residential refrigerator and freezers, general air conditioning systems, heat pumps, and the like.

Many existing refrigeration systems are currently adapted for use in connection with existing refrigerants, and the azeotrope-like compositions of the present invention are believed to be adaptable for use in many of such systems, either with or without system modification. In many applications the azeotrope-like compositions of the present invention may provide an advantage as a replacement in systems, which are currently based on refrigerants having a relatively high capacity. Furthermore, in embodiments where it is desired to use a lower capacity refrigerant composition of the present invention, for reasons of efficiency for example, to replace a refrigerant of higher capacity, such embodiments of the present compositions provide a potential advantage.

Thus, it is preferred in certain embodiments to use azeotrope-like compositions comprising, or consisting essentially of, Z-HFO-1336mzzm and one or more alcohols, as a replacement for existing refrigerants, such as HCFC-123 or HFC-134a. In certain applications, the refrigerants of the present invention potentially permit the beneficial use of larger displacement compressors, thereby resulting in better energy efficiency than other refrigerants, such as HCFC-123 or HFC-134a. Therefore the refrigerant compositions of the present invention provide the possibility of achieving a competitive advantage on an energy basis for refrigerant replacement applications.

Although it is contemplated that the azeotrope-like compositions of the present invention may include the components in widely ranging amounts, it is generally preferred that refrigerant compositions of the present invention comprise, or consist essentially of, Z-HFO-1336mzzm, in an amount that is at least about 50% by weight, and even more preferably at least about 70% by weight, of the composition.

Power Cycle Use

Rankine cycle systems are known to be a simple and reliable means to convert heat energy into mechanical shaft power. Organic working fluids are useful in place of water/steam when low-grade thermal energy is encountered. Water/steam systems operating with low-grade thermal energy (typically 400° F. and lower) will have associated high volumes and low pressures. To keep system size small and efficiency high, organic working fluids with boiling points near room temperature are employed. Such fluids would have higher gas densities lending to higher capacity and favorable transport and heat transfer properties lending to higher efficiency as compared to water at low operating temperatures. In industrial settings there are more opportunities to use flammable working fluids such as toluene and pentane, particularly when the industrial setting has large quantities of flammables already on site in processes or storage. For instances where the risk associated with use of a flammable working fluid is not acceptable, such as power generation in populous areas or near buildings, other fluids such as CFC-113 and CFC-11 were used. Although these materials were non-flammable, they were a risk to the environment because of their ozone-depletion potential. Ideally, the organic working fluid should be environmentally acceptable, non-flammable, of a low order of toxicity, and operate at positive pressures.

As used herein, the term "nonflammable" refers to compounds and compositions of the present invention which do not exhibit a flashpoint as measured by one of the standard flash point methods, for example ASTM-1310-86 "Flash point of liquids by tag Open-cup apparatus."

Organic Rankine cycle systems are often used to recover waste heat from industrial processes. In combined heat and power (cogeneration) applications, waste heat from combustion of fuel used to drive the prime mover of a generator set is recovered and used to make hot water for building heat, for example, or for supplying heat to operate an absorption chiller to provide cooling. In some cases, the demand for hot water is small or does not exist. The most difficult case is when the thermal requirement is variable and load matching becomes difficult, confounding efficient operation of the combined heat and power system. In such an instance, it is more useful to convert the waste heat to shaft power by using an organic Rankine cycle system. The shaft power can be used to operate pumps, for example, or it may be used to generate electricity. By using this approach, the overall system efficiency is higher and fuel utilization is greater. Air emissions from fuel combustion can be decreased since more electric power can be generated for the same amount of fuel input.

The process that produces waste heat is at least one selected from the group consisting of fuel cells, internal combustion engines, internal compression engines, external combustion engines, and turbines. Other sources of waste heat can be found in association with operations at oil refineries, petrochemical plants, oil and gas pipelines, chemical industry, commercial buildings, hotels, shopping malls, supermarkets, bakeries, food processing industries, restaurants, paint curing ovens, furniture making, plastics molders, cement kilns, lumber kilns (drying), calcining operations, steel industry, glass industry, foundries, smelting, air-conditioning, refrigeration, and central heating. See U.S. Pat. No. 7,428,816, the disclosure of which is hereby incorporated herein by reference.

One specific embodiment of a power cycle use of this compound is a process for recovering waste heat in an organic Rankine cycle system in which the working fluid is an azeotrope-like composition comprising, or consisting essentially of, Z-HFO-1336mzzm and one or more alcohols, preferably methanol or ethanol.

Power Cycle Example

This example demonstrates the use of the azeotrope-like compositions of the present invention for use as a Rankine power cycle composition.

Following the procedure outlined in Smith, J. M. et al., Introduction to Chemical Engineering Thermodynamics; McGraw-Hill (1996), the effectiveness of various working fluids in an organic Rankine cycle can by compared. The conditions used in the organic Rankine cycle calculations in this example are a pump efficiency of 75%, expander efficiency of 80%, boiler temperature of 190° C., condenser temperature of 45° C. and 1000 W of heat supplied to the boiler. The performance of a 95:5 wt % mixture of Z-HFO-1336mzzm:methanol is compared to the commercially available fluid HFC-245fa (available from Honeywell). The thermal efficiency of HFC-245fa and 95:5 wt % mixture of Z-HFO-1336mzzm:methanol at the conditions specified is 0.142 and 0.158, respectively. This shows that a 95:5 wt % mixture of Z-HFO-1336mzzm:methanol would perform better than HFC-245fa in a power cycle.

Cleaning and Contaminant Removal

The present invention also provides methods of removing containments from a product, part, component, substrate, or any other article or portion thereof by applying to the article an azeotrope-like composition of the present invention. For the purposes of convenience, the term "article" is used herein to refer to all such products, parts, components, substrates, and the like and is further intended to refer to any surface or portion thereof. Furthermore, the term "contaminant" is intended to refer to any unwanted material or substance present on the article, even if such substance is placed on the article intentionally. For example, in the manufacture of semiconductor devices it is common to deposit a photoresist material onto a substrate to form a mask for the etching operation and to subsequently remove the photoresist material from the substrate. The term "contaminant" as used herein is intended to cover and encompass such a photo resist material.

Preferred methods of the present invention comprise applying the present composition to the article. Although it is contemplated that numerous and varied cleaning techniques can employ the azeotrope-like compositions of the present invention to good advantage, it is considered to be particularly advantageous to use the present compositions in connection with supercritical cleaning techniques. Supercritical cleaning is disclosed in U.S. Pat. No. 6,589,355, which is assigned to the assignee of the present invention and incorporated herein by reference.

For supercritical cleaning applications, it is preferred in certain embodiments to include in the present cleaning compositions, in addition to the azeotrope-like composition of the present invention, another component, such as $CO_2$ and other additional components known for use in connection with supercritical cleaning applications.

It may also be possible and desirable in certain embodiments to use the present cleaning compositions in connection with particular sub-critical vapor degreasing and solvent cleaning methods.

Another cleaning embodiment of the invention comprises the removal of contaminants from vapor compression systems and their ancillary components when these systems are manufactured and serviced. As used herein, the term "contaminants" refers to processing fluids, lubricants, particulates, sludge, and/or other materials that are used in the manufacture of these systems or generated during their use. In general, these contaminants comprise compounds such as alkylbenzenes, mineral oils, esters, polyalkyleneglycols, polyvinylethers and other compounds that are made primarily of carbon, hydrogen and oxygen. The azeotrope-like compositions of the present invention will be useful for this purpose.

Cleaning Composition Example

This example demonstrates the use of the azeotrope-like compositions of the present invention for use as a cleaning composition.

Azeotrope-like compositions are prepared containing 95% by weight Z-HFO-1336mzzm with about 5% by weight ethanol. Several stainless steel coupons are soiled with mineral oil, rosin flux or other contaminants. Then these coupons are then immersed in the solvent blend. The blend could remove the oils in a short period of time. The coupons are observed visually for cleanliness. Similar results are expected with the other mixtures. Similar results are also expected with silicon oil.

Propellants for Sprayable Compositions

In another embodiment, the azeotrope-like compositions of this invention may be used as propellants in sprayable compositions, either alone or in combination with known propellants. The propellant composition comprises, more preferably consists essentially of, and, even more preferably, consists of the azeotrope-like compositions of the invention. The active ingredient to be sprayed together with inert ingredients, solvents, and other materials may also be present in the sprayable mixture. Preferably, the sprayable composition is an aerosol. Suitable active materials to be sprayed include, without limitation, lubricants, insecticides, cleaners, cosmetic materials such as deodorants, perfumes and hair sprays, polishing agents, as well as medicinal materials such as skin cooling agents (sunburn treatment), topical anesthetics and anti-asthma medications.

The sprayable composition includes a material to be sprayed and a propellant including the azeotrope-like compositions of this invention. Inert ingredients, solvents, and other materials may also be present in the sprayable mixture. Preferably, the sprayable composition is an aerosol. Suitable materials to be sprayed include, without limitation, cosmetic materials such as deodorants, perfumes, hair sprays, cleansers, and polishing agents as well as medicinal materials such as anti-asthma and anti-halitosis medications.

Sterilization

Many articles, devices and materials, particularly for use in the medical field, must be sterilized prior to use for the health and safety reasons, such as the health and safety of patients and hospital staff. The present invention provides methods of sterilizing comprising contacting the articles, devices or material to be sterilized with an azeotrope-like composition of the present invention, and optionally in combination with one or more additional sterilizing agents.

While many sterilizing agents are known in the art and are considered to be adaptable for use in connection with the present invention, in certain preferred embodiments sterilizing agent comprises ethylene oxide, formaldehyde, hydrogen peroxide, chlorine dioxide, ozone and combinations of these. In certain embodiments, ethylene oxide is the preferred sterilizing agent. Those skilled in the art, in view of the teachings contained herein, will be able to readily determine the relative proportions of sterilizing agent and the present compound(s) to be used in connection with the present sterilizing compositions and methods, and all such ranges are within the broad scope hereof.

As is known to those skilled in the art, certain sterilizing agents, such as ethylene oxide, are extremely flammable components, and the compound(s) in accordance with the present invention are included in the present compositions in amounts effective, together with other components present in the composition, to reduce the flammability of the sterilizing composition to acceptable levels. The sterilization methods of the present invention may be either high or low-temperature sterilization of the present invention involves the use of a compound or composition of the present invention at a temperature of from about 250° F. to about 270° F., preferably in a substantially sealed chamber. The process can be completed usually in less than about two hours. However, some articles, such as plastic articles and electrical components, cannot withstand such high temperatures and require low-temperature sterilization.

Sterilization Examples

In low temperature sterilization methods, the article to be sterilized is exposed to a fluid comprising a composition of the present invention at a temperature of from about room temperature to about 200° F., more preferably at a temperature of from about room temperature to about 100° F.

The low-temperature sterilization of the present invention is preferably at least a two-step process performed in a substantially sealed, preferably air tight, chamber. In the first step (the sterilization step), the articles having been cleaned and wrapped in gas permeable bags are placed in the chamber.

Air is then evacuated from the chamber by pulling a vacuum and perhaps by displacing the air with steam. In certain embodiments, it is preferable to inject steam into the chamber to achieve a relative humidity that ranges preferably from about 30% to about 70%. Such humidities may maximize the sterilizing effectiveness of the sterilant, which is introduced into the chamber after the desired relative humidity is achieved. After a period of time sufficient for the sterilant to permeate the wrapping and reach the interstices of the article, the sterilant and steam are evacuated from the chamber.

In the preferred second step of the process (the aeration step), the articles are aerated to remove sterilant residues. Removing such residues is particularly important in the case of toxic sterilants, although it is optional in those cases in which the substantially non-toxic compounds of the present invention are used. Typical aeration processes include air washes, continuous aeration, and a combination of the two. An air wash is a batch process and usually comprises evacuating the chamber for a relatively short period, for example, 12 minutes, and then introducing air at atmospheric pressure or higher into the chamber.

As used herein the term "non-toxic" refers to compounds and compositions of the present invention which have an acute toxicity level substantially less than, and preferably at least about 30 relative percent less than, the toxicity level of HFO-1223xd, as measured by the method published in Anesthesiology, Vol. 14, pp. 466-472, 1953, incorporated here by reference.

This cycle is repeated any number of times until the desired removal of sterilant is achieved. Continuous aeration typically involves introducing air through an inlet at one side of the chamber and then drawing it out through an outlet on the other side of the chamber by applying a slight vacuum to the outlet. Frequently, the two approaches are combined. For example, a common approach involves performing air washes and then an aeration cycle.

Lubricants

In certain preferred embodiments, the azeotrope-like compositions of the present invention can further comprise a lubricant. Any of a variety of conventional lubricants may be used in the azeotrope-like compositions of the present invention. An important requirement for the lubricant is that, when in use in a refrigerant system, there must be sufficient lubricant returning to the compressor of the system such that the compressor is lubricated. Thus, suitability of a lubricant for any given system is determined partly by the refrigerant/lubricant characteristics and partly by the characteristics of the system in which it is intended to be used.

Examples of suitable lubricants include mineral oil, alkyl benzenes, polyol esters, including polyalkylene glycols, PAG oil, and the like. Mineral oil, which comprises paraffin oil or naphthenic oil, is commercially available. Commercially available mineral oils include Witco LP 250 (registered trademark) from Witco, Zerol 300 (registered trademark) from Shrieve Chemical, Sunisco 3GS from Witco, and Calumet R015 from Calumet. Commercially available alkyl benzene lubricants include Zerol 150 (registered trademark). Commercially available esters include neopentyl glycol dipelargonate which is available as Emery 2917 (registered trademark) and Hatcol 2370 (registered trademark). Other useful esters include phosphate esters, dibasic acid esters, and fluoroesters. Preferred lubricants include polyalkylene glycols and esters. Certain more preferred lubricants include polyalkylene glycols.

Extraction of Flavors and Fragrances

The azeotrope-like compositions of the present invention also provide advantage when used to carry, extract or separate desirable materials from biomass. These materials include, but are not limited to, essential oils such as flavors and fragrances, oils which may be used as fuel, medicinals, nutraceuticals, etc.

Extraction Example

The suitability of the azeotrope-like compositions of the present invention for this purpose is demonstrated by a test procedure in which a sample of Jasmone is put into a heavy walled glass tube. A suitable amount of the azeotrope-like composition of the present invention is added to the glass tube. The tube is then frozen and sealed. Upon thawing the tube, when the mixture has one liquid phase containing Jasmone and the azeotrope-like composition; this test establishes the favorable use of the composition as an extractant, carrier or part of delivery system for flavor and fragrance formulations, in aerosol and other formulations. It also establishes its potential as an extractant of flavors and fragrances, including from plant matter.

Flammability Reduction Methods

According to certain other preferred embodiments, the present invention provides methods for reducing the flammability of fluids, said methods comprising adding an azeotrope-like composition of the present invention to said fluid. The flammability associated with any of a wide range of otherwise flammable fluids may be reduced according to the present invention. For example, the flammability associated with fluids such as ethylene oxide, flammable hydrofluorocarbons and hydrocarbons, including: HFC-152a, 1,1,1-trifluoroethane (HFC-143a), difluoromethane (HFC-32), propane, hexane, octane, and the like can be reduced according to the present invention. For the purposes of the present invention, a flammable fluid may be any fluid exhibiting flammability ranges in air as measured via any standard conventional test method, such as ASTM E-681, and the like.

Any suitable amounts of the present compounds or compositions may be added to reduce flammability of a fluid according to the present invention. As will be recognized by those of skill in the art, the amount added will depend, at least in part, on the degree to which the subject fluid is flammable and the degree to which it is desired to reduce the flammability thereof. In certain preferred embodiments, the amount of compound or composition added to the flammable fluid is effective to render the resulting fluid substantially non-flammable.

Flammability Reduction Example

This example demonstrates the use of the azeotrope-like compositions of the present invention for reduction of flammability of another composition.

In an ASTM E681 apparatus at ambient conditions, one mixes isopentane vapor and the azeotrope like mixture of 97:2 wt % Z-HFO-1336mzzm:ethanol to find that the lower flammability limit (LFL) increases as more of the azeotrope like mixture of 97:2 wt Z-HFO-1336mzzm:ethanol is added. This indicates lower flammability for the blend than that of the isopentane by itself leading; a less flammable material which is easier to use safely. This higher LFL allow higher concentration in air without concern for ignition source and potential fires or explosions.

Two aerosol cans are filled with methanol/water and one is pressurized with HFC-152a while the other is pressurized with HFC-152a and an azeotrope like mixture of 97:2 wt Z-HFO-1336mzzm:ethanol. When the aerosols from the cans are sprayed over and into a candle flame as in the aerosol flame extension test procedure one observe less flame extension from the can that is pressured with an azeotrope like mixture of 97:2 wt % Z-HFO-1336mzzm:ethanol.

Flame Suppression Methods

The present invention further provides methods of suppressing a flame, said methods comprising contacting a flame with an azeotrope-like composition of the present invention. If desired, additional flame suppressing agents can also be used with the composition of the present invention, either in admixture, or as a secondary flame suppressing agent. One class of compounds useful for this purpose is the fluoroketones. One especially preferred fluoroketone is dodecafluoro-2-methylpentan-3-one. One commercial source for this preferred compound is the 3M Company under the trade name Novec 1230.

Any suitable methods for contacting the flame with the present composition may be used. For example, a composition of the present invention may be sprayed, poured, and the like onto the flame, or at least a portion of the flame may be immersed in the composition.

While the present invention has been particularly shown and described with reference to preferred embodiments, it will be readily appreciated by those of ordinary skill in the art that various changes and modifications may be made without departing from the scope of the invention. It is intended that the claims be interpreted to cover the disclosed embodiment, those alternatives which have been discussed above and all equivalents thereto.

What is claimed is:

1. An azeotrope composition comprising effective amounts of cis-1,1,1,4,4,4-hexafluoro-2-butene (Z-HFO-1336mzzm) and a second component consisting of HCFO-1233zd(E), wherein HCFO-1233zd(E) is provided in an amount from about 83.6 wt % to less than 100 wt %.

2. The azeotrope or azeotrope-like composition of claim 1 comprising from about 93 wt % to less than 100 wt % of HCFO-1233zd(E) and from greater than about 0 wt % to about 7 wt % of Z-HFO-1336mzzm.

3. The azeotrope or azeotrope-like composition of claim 1 comprising from about 97 wt % to less than 100 wt % of Z-HFO-1336mzzm and from greater than about 0 wt % to about 3 wt % of HCFO-1233zd(E).

4. The azeotrope or azeotrope-like composition of claim 1 having a boiling point of about 17.7° C.±0.5° C. at a pressure of about 14.5 psia.

* * * * *